United States Patent
Califano et al.

(10) Patent No.: US 7,860,660 B2
(45) Date of Patent: Dec. 28, 2010

(54) CHARACTERIZATION OF PHENOTYPES BY GENE EXPRESSION PATTERNS AND CLASSIFICATION OF SAMPLES BASED THEREON

(75) Inventors: Andrea Califano, New York, NY (US); Gustavo A. Stolovitzky, Bronx, NY (US); Yuhai Tu, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/574,195

(22) Filed: Oct. 6, 2009

(65) Prior Publication Data

US 2010/0023273 A1    Jan. 28, 2010

Related U.S. Application Data

(62) Division of application No. 09/841,580, filed on Apr. 24, 2001, now abandoned.

(60) Provisional application No. 60/237,590, filed on Oct. 3, 2000.

(51) Int. Cl.
*G06F 19/00* (2006.01)
*G06F 17/18* (2006.01)
*G01N 31/00* (2006.01)

(52) U.S. Cl. .................. 702/19; 702/32; 702/179

(58) Field of Classification Search .................... None
See application file for complete search history.

(56) References Cited

PUBLICATIONS

Alizadeh (2000) Nature vol. 403, Feb. 3, pp. 503-511.*
Alon (1999) PNAS vol. 96, June pp. 6745-6750.*
Ben-Dor (1999) Journal of Computational Biology, vol. 6, pp. 281-297.*
Brown (2000) PNAS vol. 97, January pp. 262-267.*
DeRisi (1996) Nature Genetics vol. 14, December pp. 457-460.*
Golub (1999) Science vol. 286, October pp. 531-537.*
Kerr (2000) Journal of Computational Biology vol. 7, pp. 819-837.*
Ross (2000) Nature Genetics vol. 24, March pp. 227-235.*
Tamayo (1999) PNAS vol. 96, March pp. 2907-2912.*

* cited by examiner

*Primary Examiner*—Lori A Clow
(74) *Attorney, Agent, or Firm*—Ryan, Mason & Lewis, LLP

(57) ABSTRACT

Generally, the present invention applies a transformation to convert a probability distribution of gene expression signals in control samples to a uniform distribution. The uniform distribution allows better comparisons between expression levels for genes. The transformation is derived from gene expression signals of control data, and is applied to gene expression signals of phenotype data. The phenotype data can be represented in a matrix format. A number of gene expression patterns may be determined (in the form of submatrices) that will characterize the phenotype. The uniform distribution helps in this regard, as it allows better comparisons of patterns. The gene expression patterns can then be used to classify samples as belonging to the phenotype set. Preferably, a discriminant function is used to compare a sample with the gene expression patterns that characterize the phenotype. The discriminant function can determine a score that can be used to determine whether the sample belongs to the phenotype.

20 Claims, 10 Drawing Sheets

*FIG. 5*

|  | GENE$_1$ | GENE$_2$ | ... | GENE$_{N_g}$ |
|---|---|---|---|---|
| EXP$_1$ | U$_{11}$ | U$_{21}$ | ... | U$_{g1}$ |
| EXP$_2$ | U$_{12}$ | U$_{22}$ | ... | U$_{g2}$ |
| ⋮ | ⋮ | ⋮ |  | ⋮ |
| EXP$_{N_e}$ | U$_{1e}$ | U$_{2e}$ | ... | U$_{ge}$ |

*FIG. 6*

|  | GENE$_1$ | GENE$_2$ | GENE$_3$ | GENE$_4$ | GENE$_5$ |
|---|---|---|---|---|---|
| EXP$_1$ | 0.1 | 0.3 | 0.6 | 0.7 | 0.8 |
| EXP$_2$ | 0.1 | 0.2 | 0.5 | 0.7 | 0.5 |
| EXP$_3$ | 0.1 | 0.2 | 0.1 | 0.9 | 0.6 |
| EXP$_4$ | 0.1 | 0.2 | 0.5 | 0.6 | 0.6 |

← N$_g$ →, ↕ N$_e$ $$V_{G,E} = \begin{bmatrix} 0.1 & 0.6 & 0.7 \\ 0.1 & 0.5 & 0.7 \\ 0.1 & 0.5 & 0.6 \end{bmatrix}$$

CHARACTERIZATION OF PHENOTYPES BY GENE EXPRESSION PATTERNS AND CLASSIFICATION OF SAMPLES BASED THEREON

CROSS-REFERENCE TO RELATED APPLICATIONS

This application is a divisional application of U.S. patent application Ser. No. 09/841,580, filed on Apr. 24, 2001 now abandoned, which claimed the benefit of U.S. Provisional Application No. 60/237,590, filed Oct. 3, 2000, both of which are incorporated by reference herein.

FIELD OF THE INVENTION

The present invention relates to genotypes and phenotypes and, more particularly, relates to the characterization of phenotypes by gene expression patterns and classification of samples based thereon.

BACKGROUND OF THE INVENTION

Gene expression microarrays are becoming very important devices, as they allow researchers to test large quantities of genetic material. These devices are important because they allow researchers to analyze cells, and the genetic information of the cells, to determine whether the cells belong to particular phenotypes. A phenotype is the determinable characteristics of an organism, as determined by genes and the relationship of the genes to the environment. Researchers are currently examining such phenotypes as cancer, diabetes and other diseases. Gene expression microarrays are increasing in importance in this research.

There are different gene expression microarray technologies. In typical implementations, gene expression microarrays contain thousands of DeoxyriboNucleic Acid (DNA) molecules that represent many genes. These DNA molecules are placed on discrete spots on the microarray. Each of these DNA molecules may be thought of as part of an "unzipped" piece of a gene that is waiting for a complement to which it will be "zipped." The DNA molecules attached to the microarrays are commonly called probes.

The complements, also called targets, generally come from messenger RiboNucleic Acid (mRNA), which are basically the working copies of genes within cells. When testing a cell from an organism, the mRNA from a particular sample is purified and a marker is attached to it. The mRNA is added to the gene expression microarray and the mRNA "hybridizes" with the DNA to which it is a complement. Thus, some of the discrete spots will contain mRNA hybridized to DNA, and other spots will not contain mRNA hybridized to DNA. For clarity, "targets" will be referred to as mRNA herein. In some technologies, however, the cellular mRNA is reverse-transcribed into complementary DNA (cDNA), which are complementary copies of otherwise fragile mRNA. The cDNA is linearly amplified and is subsequently used to hybridize with the probes.

The marker attached to the mRNA is used to determine which spots contain mRNA hybridized to DNA. Usually, the markers are fluorescent molecules that fluoresce when a laser light of an appropriate frequency and power shines on them. This fluorescence can be measured.

The fluorescence is a measure of how much a gene "expresses" itself. If there is a high fluorescence for a particular gene, this means that the gene is very active. Conversely, if there is low or no fluorescence for a gene, this means that the gene is inactive. Thus, by examining the fluorescence of the microarray, researchers can determine the degree of activity of the different genes.

This method is advantageous in that it is possible to determine gene function for tissue affected by a disease as compared to tissue not affected by such disease. By comparing the two phenotypes, researchers can in principle determine which genes contribute to certain diseases and how they contribute.

When making these determinations, it is helpful to examine genes from diverse groups of both people who have a disease and people who do not have this disease (hereafter called "healthy," even though they may be affected by other conditions). Because people are different, there will be differences in the expression level of genes between subjects in the group. These differences occur in both healthy and sick individuals. These differences will be apparent during microarray analysis of samples for the various people in the group. For instance, one person could have an enzymatic deficiency (unrelated to the disease under study) which causes a set of genes to be less expressive. Another person may not have such deficiency and his or her corresponding genes express themselves at a much higher level. Therefore, even for healthy people, there is a variation in gene expression.

Because of these variations, which are further compounded with errors in the experimental measurements, usually many microarray samples are taken and analyzed. The microarray results from this data can be used to make statistical analyses with the aim of comparing sick cells and their genes with healthy cells and their genes. From these analyses, researchers attempt to determine which genes actually relate to the disease.

One method of determining this is to look for patterns in the data. For example, perhaps one particular gene is turned on in a sick cell, while another gene is turned off. This "pattern" can be determined because the expression of one gene will be low, while the expression of another gene will be high. Moreover, as previously discussed, the researchers generally compare the expressions from the genes of the unhealthy phenotype with the expressions from the genes with the healthy phenotype. It helps to compare genes from unhealthy cells with genes from healthy cells, as the healthy cells provide a baseline. For instance, perhaps a certain gene is almost always turned on in normal cells. Even though a cell exhibiting an unhealthy phenotype might also have this gene turned on, because normal cells also have this gene turned on, it is likely that this gene does not relate to the disease being researched. However, if the unhealthy cell has this gene turned off and healthy cells generally have this cell turned on, then it could be that this gene does relate to the disease being researched.

There are various ways of analyzing gene expression data. For a recent review on the methods, see "Genetic Network Inference: From Co-expression Clustering to Reverse Engineering," Bioinformatics, August 2000, 16(8), 707-26, the disclosure of which is incorporated by reference herein. Most of these methods analyze the fluorescent outputs for a number of samples of a gene to determine an "average" fluorescence for the gene. These values are indicative of the expression level of a gene. With a number of different genes, a "pattern" of these expression level averages can be made. Typically, however, the fluorescence of a given gene across several experiments can vary tremendously. In this situation, the determined average is meaningless. Some researchers attempt to alleviate this problem by determining the average fluorescence value for a particular gene, evaluating the standard deviation of the fluorescence value for the variety of samples for the gene and, from this data, determining a normalized distribution in which the standard deviation is one. The limitation of this method is that it treats genes as independent, neglecting the natural correlations between genes.

Thus, what is needed is a way of comparing expressions from samples being examined with expression levels from control samples and a better way of detecting gene-gene correlations when searching for patterns.

SUMMARY OF THE INVENTION

Generally, the present invention applies a transformation to convert a probability distribution of gene expression signals in control samples to a uniform distribution. The uniform distribution allows better comparisons between expression levels for genes. The transformation is derived from gene expression signals of control data, and is applied to gene expression signals of phenotype data. The phenotype data can be represented in a matrix format. A number of gene expression patterns may be determined (in the form of submatrices) that will characterize the phenotype. The uniform distribution helps in this regard, as it allows better comparisons of patterns. The gene expression patterns can then be used to classify samples as belonging to the phenotype set. Preferably, a discriminant function is used to compare a sample with the gene expression patterns that characterize the phenotype. The discriminant function can determine a score that can be used to determine whether the sample belongs to the phenotype.

A more complete understanding of the present invention, as well as further features and advantages of the present invention, will be obtained by reference to the following detailed description and drawings.

BRIEF DESCRIPTION OF THE DRAWINGS

FIG. 5 illustrates a phenotype matrix prior to transformation, in accordance with one embodiment of the present invention;

FIG. 6 illustrates an exemplary phenotype matrix after transformation, in accordance with one embodiment of the present invention;

DETAILED DESCRIPTION OF EMBODIMENTS

Basically, the present invention is used to take an initial set of expression data for one phenotype (generally called the control set and containing information from healthy cells) and to determine transformations from this data. The transformations are applied to a set of expression data from another phenotype (generally called the phenotype set and containing information from unhealthy cells). The transformed set of data is used to determine gene expression patterns that are characteristic of the phenotype. New expression data from samples that have an unknown genetic makeup are compared with the gene expression patterns. Based on this comparison, the new samples are classified as belonging to one of the two phenotypes.

Figure 1:
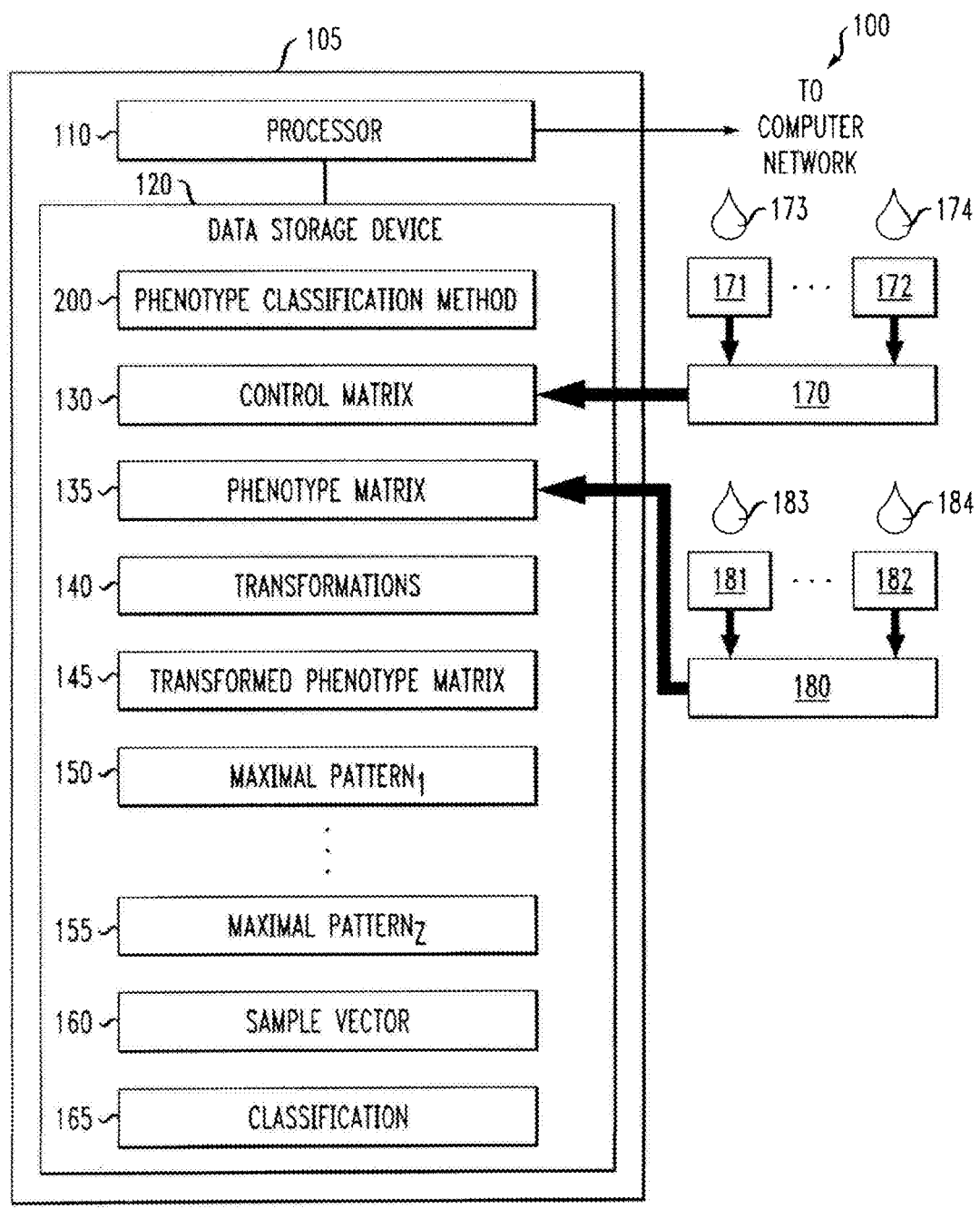
FIG. 1 is a computer system for characterization of phenotypes by gene expression patterns and classification of samples based thereon, in accordance with one embodiment of the present invention.

Turning now to FIG. 1, this figure shows a block diagram of a system 100 for characterization of phenotypes by gene expression patterns and classification of samples based thereon. System 100 comprises a computer system 105 that comprises processor 110 and a data storage device 120. System 100 also comprises gene micro arrays or chips 171, 172, 181, and 182, microarray processing devices 170, 180, and biological material 173, 174, 183, and 184. Data storage device 120 comprises a phenotype classification method 200, a control matrix 130, a phenotype matrix 135, transformations 140, a transformed phenotype matrix 145, maximal patterns 150 through 155, sample vector(s) 160 and classification(s) 165.

The personal computer 105 comprises a processor 110 operatively coupled to the data storage device 120. Data storage device 120 will configure the processor 110 to implement the methods, steps, and functions disclosed herein. The data storage device could be distributed or local and the processor could be distributed or singular. The data storage device could be implemented as an electrical, magnetic or optical memory, or any combination of these or other types of storage devices.

Biological materials 173 through 174 are deposited onto gene microarrays 171 through 172. As is known in the art, the biological materials 173 through 174 contain a marker or markers (not shown in FIG. 1) that can be used to determine how much each gene probed on gene microarrays 171 through 172 expresses itself in biological materials 173 through 174. Generally, the biological materials 173 through 174 are derived from cells of organisms and are usually purified messenger RiboNucleic Acid (mRNA). Microarray processing device 170 processes the gene microarrays 171 through 172, of which there are a sufficient number to provide a probability density. The microarray processing device 170 produces a number for each gene of each gene micro array of microarrays 171 through 172, and this number is related to the expression level of the gene. Similarly, biological materials 183 through 184 are deposited onto gene microarrays 181 through 182. Biological materials 183 through 184 contains a marker or markers (not shown in FIG. 1) that can be used to determine how much each gene probed on gene microarrays 181 through 182 expresses itself in the biological samples 183 through 184. Generally, the biological materials 183 through 184 are derived from cells of organisms and are usually purified messenger RiboNucleic Acid (mRNA). Microarray processing device 180 processes the gene microarrays 181 through 182. Usually, biological materials 173 through 174 contain materials from healthy cells, while biological materials 183 through 184 contain information from unhealthy cells or cells from an organism that has a certain disease or condition.

Generally, the data from micro array processing devices 170 and 180 are formed into matrices 130 and 135. Usually, biological material is processed at one location and the data in the matrices 130, 135 is processed at another location. However, it is possible to perform both steps at one location, as FIG. 1 shows.

Figure 2:
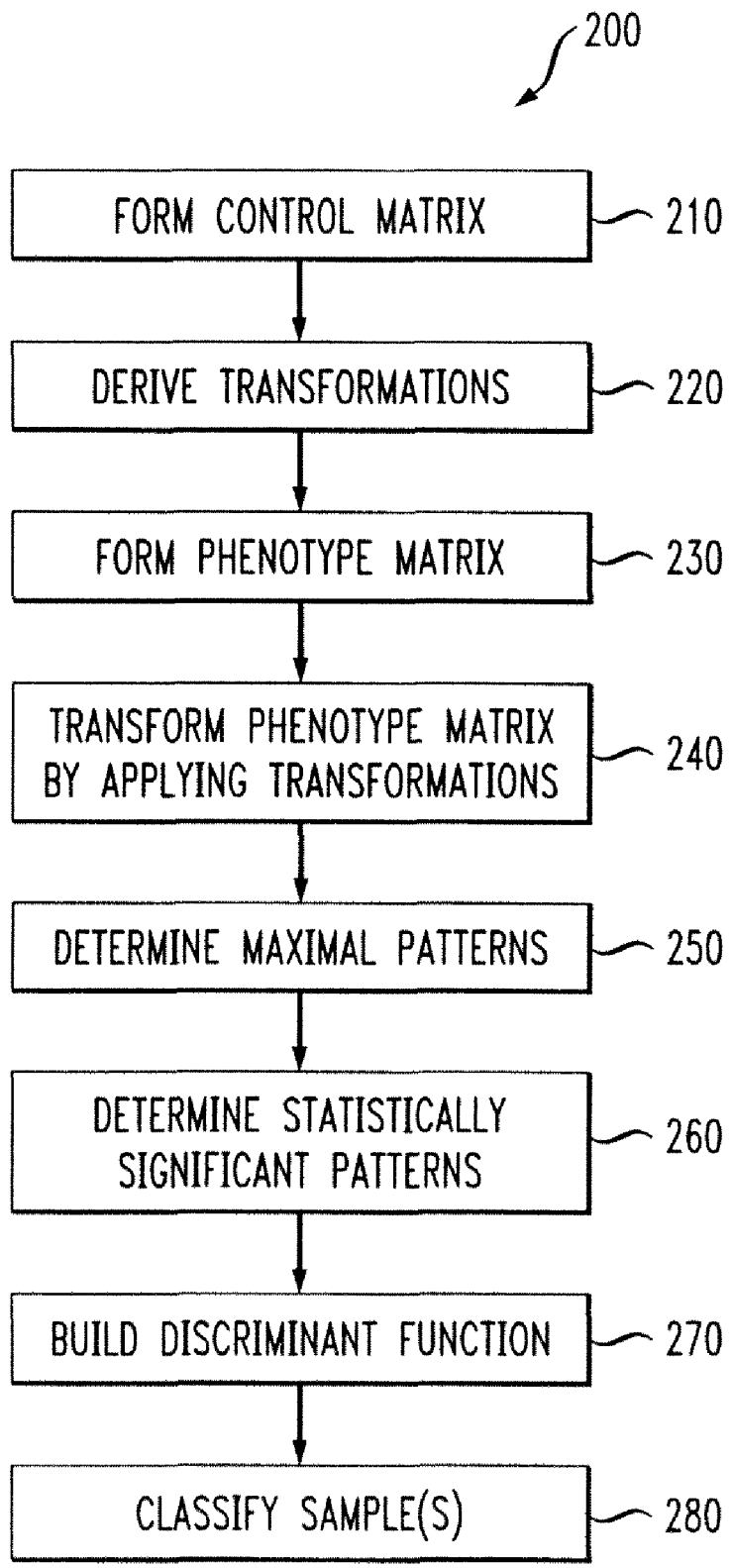
FIG. 2 is a block diagram of a method for characterization of phenotypes by gene expression patterns and classification of samples based thereon, in accordance with one embodiment of the present invention.

Phenotype classification method 200, shown in FIG. 2, determines transformations 140 from control matrix 130. Control matrix 130 is a matrix of experimental data from control samples. Generally, such control samples will be samples of messenger RiboNucleic Acid (mRNA) from healthy cells taken from a variety of individuals. However, there is no requirement that these samples come from healthy cells or from a variety of individuals, and other types of cells or homogeneous samples may be used. The control matrix 130 preferably contains columns corresponding to particular genes and rows corresponding to particular experiments. Each column of the matrix is used to determine one transformation of transformations 140. Each column of the matrix will contain a number of expressions from one gene. These expressions will be distributed in a particular manner. Such probability distributions indicate how probable it is that a gene expressed itself at a particular value. These values are generally based on the amount of luminescence detected from certain points on a gene microarray. Each transformation preferably converts a distribution to a uniform distribution.

To transform the probability distribution to a uniform distribution, an integral of the probability density function is performed. The integral may be numerically performed directly on the probability density function data. Alternatively, an equation for the probability density function may be derived and the method will use the equation when integrating.

The transformations 140 are applied to the corresponding elements of the phenotype matrix 135. Phenotype matrix 135 preferably contains columns corresponding to genes and rows corresponding to experimental expressions. Each element of the phenotype matrix 135 is converted from its current expression value to another value. To determine the second value, a transformation for the gene is used. This is explained in more detail below, in reference to FIG. 4 and other figures.

After transformation, transformed phenotype matrix 145 occurs. It is not necessary to have a separate matrix from phenotype matrix 135; instead, each element of phenotype matrix 135 can be transformed and replace the original element. However, a transformed phenotype matrix 145 is shown in FIG. 1 for clarity. Method 200 will search the transformed phenotype matrix 145 for patterns and determine maximal patterns 150 through 155. Generally, there will be one or more of the maximal patterns 150 through 155. The maximal patterns can be used, preferably as part of a discriminant function, when examining sample vector(s) 160 to determine the classification(s) 165 of the vectors. The maximal patterns may be thought of as gene expression patterns. The classification indicates whether the sample vector is part of the phenotype matrix or part of the control matrix. Optionally, additional processing may be used to eliminate some of the maximal patterns and create a subset of the gene expression patterns that are better indicators of the phenotype.

It should be noted that FIG. 1 may have fewer or more components than what are shown. For example, when determining maximal patterns, it may be beneficial to store intermediate patterns. These intermediate patterns are not shown in FIG. 1. Similarly, once maximal patterns 150 through 155 are determined, the control matrix 130, phenotype matrix 135, transformations 140, and transformed phenotype matrix 145 could be discarded. Sample vector 160 and 165 might not reside in data storage device 120 while, for instance, control matrix 130 resides in data storage device 120.

As is known in the art, the methods and apparatus discussed herein may be distributed as an article of manufacture that itself comprises a computer readable medium having computer readable code means embodied thereon. The computer readable program code means is operable, in conjunction with a computer system such as computer system 105, to carry out all or some of the steps to perform the methods or create the apparatuses discussed herein. The computer readable medium may be a recordable medium (e.g., floppy disks, hard drives, compact disks, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic media, or height variations on the surface of a compact disk.

Before proceeding to a more detailed discussion of method 200, it is helpful to discuss the following definitions that will be used in this disclosure.

Gene Expression Matrix: The result of a DNA microarray experiment is a collection of gene expression levels, the level for each gene being roughly proportional to the concentration of the mRNA transcribed from that particular gene in the cell. $N_g$ is the number of different gene probes in the microarray. $N_e$ is the number of microarray samples (i.e., experiments or cells). Thus, a set of DNA microarray experiments is conveniently represented by an $N_e \times N_g$ gene expression matrix $V=\{v_{eg}\}$, where e is the experiment index and g is the gene index. In this instance, each $v_{eg}$ is a transformed expression level according to Equation (1) of the g-th gene in the e-th sample. If the set is the control set, then the transformed gene expression values $v_{eg}$ will be approximately uniformly distributed. The term gene expression matrix can thus refer to both transformed and not-transformed expression matrices.

Gene vector and Experiment vector: A list of gene identifications $G=\{g_1, \ldots g_k\}$, with $1 \leq g_1 < g_2 < \ldots < g_k \leq N_g$ is called a gene vector. A list of experiments $E=\{e_1, \ldots, e_j\}$, with $1 \leq e_1 < e_2 < \ldots < e_j \leq N_e$ is an experiment vector.

δ-valid jk-patterns: Let V be a gene expression matrix, then a gene vector G and an experiment vector E uniquely define a j×k submatrix $VE, G=\{v_{e_i g_m}\}$ of V. Given $\delta > 0$, $V_{G,E}$ is a δ-valid jk-pattern if each column is tightly clustered in an interval of size up to δ. By this, it is meant that the maximum and the minimum value of each column must differ by less than delta. The length of the experiment vector j is called the support of the jk-pattern. If .delta. is small, each gene in a jk-pattern is expressed at approximately the same level across all the experiments in the experiment vector. However, because these are transformed values, the actual gene expression interval may be large.

Maximal patterns: A δ-valid jk-pattern is maximal if the following two conditions hold: (1) it cannot be extended into a δ-valid jk'-pattern, with k'>k, by adding genes to its gene vector, and (2) it cannot be extended into a δ-valid j'k-pattern, with j'>j, by adding experiments to its experiment vector.

Turning now to FIG. 2, this figure shows a method 200 for characterization of phenotypes by gene expression patterns and classification of samples based thereon. The method is used whenever it is desired that expression data from a control set be analyzed, expression data from a phenotype set be analyzed, and samples classified according to whether they belong to the control or phenotype set.

The method begins in step 210, when a control matrix is formed. A control matrix will preferably contain columns that correspond to specific genes and rows that correspond to experimental samples. The samples used will usually belong to one specific phenotype. Generally, the experimental samples will be from a variety of healthy cells, such that the phenotype is "normal" or "healthy." Such phenotypes may be called "cell phenotypes," which is a term generally used to indicate a common property of a set of cells. For instance, a cancer morphology, such as melanoma, is a typical cell phenotype. More subtle cell phenotypes are also possible and useful. For example, there is a "p53 phenotype" that identifies cancer cells with mutations in the p53 tumor suppressor gene. Also, by measuring the drug concentration required to inhibit by 50% the cell line growth, the so-called $GI_{50}$, it is possible to define a drug-sensitivity phenotype. The latter can be used to divide cells in two groups: one with cells that are inhibited by low concentrations of the drug (i.e., that are highly sensitive to it) and the other with cells that require high concentrations (i.e., that are resistant to it). A classification method can then be used to predict whether an unknown cell line is likely to be sensitive or resistant to a given drug.

Some complex phenotypes, such as the p53-related one, are likely to be mixtures of simpler unknown sub-phenotypes at the molecular level, each one characterized by a possibly independent pattern. Methods that rely on a single model are likely to perform poorly with these complex cases, as truly there is no single model that describes the entire set.

Figures 3, 4:
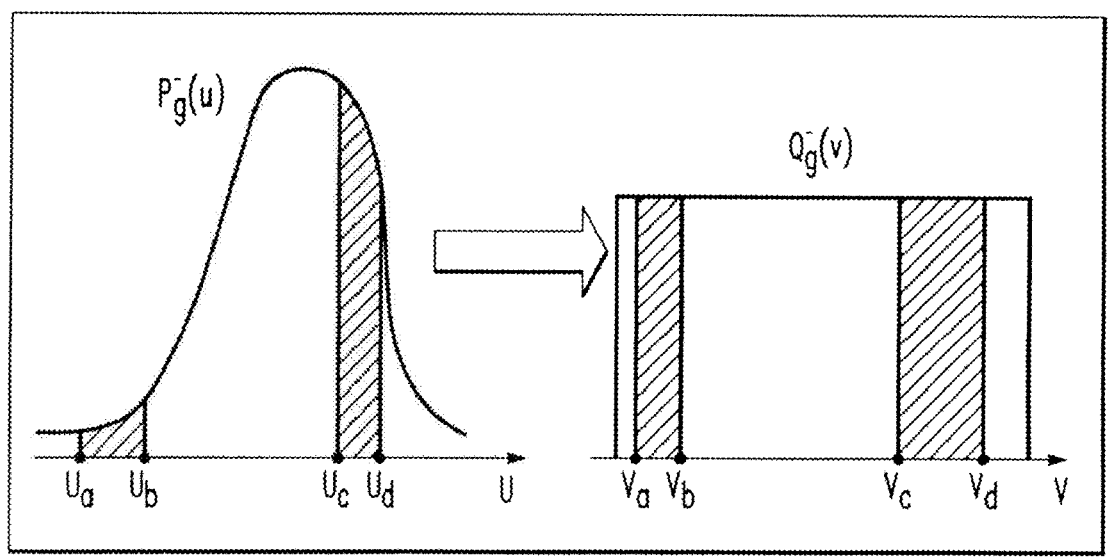
FIG. 3 illustrates a control matrix in accordance with one embodiment of the present invention.
FIG. 4 illustrates a transformation from a probability density of control samples to a uniform probability density in accordance with one embodiment of the present invention.

An exemplary control matrix is shown in FIG. 3, to be discussed below. Each column of the control matrix will preferably contain a number of expressions from a number of experiments. As is known in the art, each expression corresponds to how much or how little a particular gene is being expressed. Primarily, the expression levels are determined by examining the fluorescence of locations on a microarray. This fluorescence is converted to a number based on a number of factors, such as the optical system being used, the fluorescent markers being used, and the scanner used to convert the fluorescence into a mathematical representation. Although fluorescence is the primary readout for microarrays, other readouts, such as probeless readouts that use electrophoresis or conductance may be used.

Suppose that the expression level u of the g-th gene in the control set is distributed according to a given probability density $P_g^-(u)$. This density is estimated empirically A sufficient number of samples is required to measure this density with a sufficient degree of accuracy. Each of the columns of a control matrix should be able to determine a probability density for the gene to which the column corresponds.

In FIG. 4, discussed below, a possible shape for $P_{-g}$ is plotted. Basically, the similarity metric of the present invention tries to provide a better determination of clusters of expressions in order to provide a higher probability that two expressions are related. This is discussed in more detail in reference to FIG. 4. The present invention renormalizes the expression axis so that the distance between two points on the new axis is equal to the integral of the $P_g^-(u)$ in the previous coordinate system. This is accomplished by defining a new variable v obtained by transforming the original variable u with the following, gene-specific non-linear transformation $f_g$:

$$v = f_g(u) = \int_{-\infty}^{u} P_g^-(x)\,dx. \tag{1}$$

In this new variable, the corresponding probability density $Q_g^-(v)$ for the control set is uniformly distributed and normalized in the interval [0,1]. If $v=f_g(u)$ and $v'=f_g(u')$ are two transformed expression values, the Euclidean metric in v will be taken as a measure of similarity, or distance, between u and u':

$$D(u, u') = |v - v'| = \left| \int_{-\infty}^{u} P_g^-(x)\,dx \right|. \tag{2}$$

In other words, the distance between two expression values is chosen to be equal to the integral of the gene expression probability density in the control set between these two values. Since the number of measurements in the control set that fall between u and u' and is proportional to the integral in Equation (2), it follows that the larger the number of measurements in the control set that fall between two values, the further apart they are in the new coordinate system, and vice versa.

One significant advantage of this is that, since the probability density for all genes in the control set is uniformly distributed in the transformed space over the interval [0,1], it is now possible to analytically compute the statistics of the patterns discovered in the control set. Under previous systems, the statistics of the patterns were much harder to calculate.

In step 220 of FIG. 2, transformations are derived. One exemplary transformation is shown in FIG. 4. Each transformation takes a probability density distribution for one of the columns of the control matrix and transforms this to a uniform probability density. During this process, the actual probability density distribution may be integrated, or a function derived that estimates the actual probability density distribution and that is then integrated. This is discussed in more detail in reference to FIGS. 4, 9, and 10. The transformation may be thought of as a non-linear similarity metric, which maximizes the probability of discovering discriminative gene expression patterns.

In step 230, a phenotype matrix is formed. The phenotype matrix preferably has columns corresponding to particular genes and rows corresponding to particular experiments. Each entry is an expression level of a particular gene and a particular experiment. Generally, the experiments are from cells that exhibit a certain disease phenotype, such as cancer or diabetes. An exemplary phenotype matrix is shown in FIG. 5.

The previously determined transformations are applied to the phenotype matrix in step 240. Each transformation corresponds to one of the genes and is used to convert the expression levels of entries that correspond to the gene to a transformed value. The transformed value, as part of a transformed phenotype matrix, can be used to determine patterns. An exemplary transformed matrix is shown in FIG. 6.

Of all the possible patterns in a phenotype matrix, some of the patterns will be maximal. These maximal patterns are submatrices of the phenotype matrix. In step 250, these maximal patterns are determined. There are a variety of well known pattern-finding algorithms and techniques that may be used in this step.

For instance, the SPLASH algorithm may be used. Full details of the SPLASH algorithm are given in Califano, A., "SPLASH: Structural Pattern Localization Algorithm by Sequential Histograming," Bioinformatics 16, 341-357, 2000, the disclosure of which is incorporated by reference herein. In that paper, SPLASH was introduced as an algorithm to discover patterns in strings, where all possible relative strings alignment are allowed. Also, a density constraint is introduced to limit the impact of random matches occurring over large distances on the string. For the equivalent association discovery problem, relevant in this context, the approach is analogous, as each row in the matrix is equivalent to a string. However, the strings are prealigned in the present case, meaning that the strings are aligned with the genes to which they correspond. In addition, the density constraint criteria introduced in the SPLASH paper is no longer meaningful here, as the first and last genes are as likely to form patterns as two corresponding to contiguous matrix columns.

Using the notation of SPLASH, the canonical seed set $P_s$ has a single pattern with no genes, all the rows, and an offset of 0 for each row. The histogram operator $T_h$ is implemented by simply sorting the values in each column and then selecting all subsets of continuous values that are δ-valid. Non-maximal subsets that are completely contained within another subset are removed. Each subset is a potential super-pattern of a maximal pattern. The enumerate operator $T_e$ is then applied iteratively to create all possible maximal combinations of these superpatterns. As a result, all patterns that exist in the data are generated hierarchically by combining together smaller superpatterns, with fewer genes. Non-maximal branches are eliminated at each iteration, as soon as their corresponding superpattern arises. This contributes to the efficiency of the algorithm.

Another pattern-searching technique that may be used with the present invention is the Teiresias algorithm. This algorithm is described in Floratos et al., U.S. Pat. No. 6,108,666, "Method and Apparatus for Pattern Discovery in 1-Dimensional Systems"; Floratos et al., U.S. Pat. No. 6,092,065, "Method and Apparatus for Discovery, Clustering and Classification of Patterns in 1-Dimensional Event Streams"; Rigoutsos and Floratos, "Combinatorial Pattern Discovery in Biological Sequences: the Teiresias Algorithm," Bioinformatics, 14(1):55-67, 1998; and Rigoutsos and Floratos, "Motif Discovery Without Alignment Or Enumeration," Proceedings 2nd Annual ACM International Conference on Computational Molecular Biology, New York, N.Y., March 1998, the disclosures of which are incorporated by reference herein.

In step 260, statistically significant patterns are determined. This is an optional, but preferred step. When gene expression values are organized in a gene expression matrix, jk-patterns may occur for any given value of δ. An important determination to be made is whether any of these patterns can occur merely by chance.

An important observation is in order at this juncture: It is not meant that the expression values of different genes in "real" gene-expression matrices are independent random variables. Rather, this model is used as the null hypothesis of a statistical framework precisely to identify any skew or co-regulation in the phenotype set. This null hypothesis definition is based on two assumptions: (a) that the probability densities for the expression levels of each gene are the same as in the control set, and (b) that the gene expression levels in different experiments and/or those of different genes are independently distributed. When discovering patterns in the phenotype set, the statistically relevant patterns will be those for which the null hypothesis is rejected. These are patterns whose constituent genes are either distributed differently in the phenotype set than in the control set, and/or are expressed in a correlated fashion. Both of these features are actually the kind of behavior that we are seeking to differentiate the two sets.

Those skilled in the art will note that many genes are not independently distributed in the control set. Therefore, patterns may arise that reject the null hypothesis and yet are likely to occur in the control set. These patterns will be called promiscuous patterns. Promiscuous patterns, are easily eliminated in a post-processing phase, described in reference to step 270 below, and do not contribute significantly to remaining analysis. This is verified by experimental results given below, where any correlation in the control set is artificially removed.

An important result on the statistics of patterns is the following: given δ>0, an $N_e \times N_g$ gene expression matrix V, a k-dimensional gene vector G and a j-dimensional experiment vector E, the probability that the submatrix $V_{G,E}$ is a maximal δ-valid jk-pattern is:

$$P_\delta(j,K,N_e,N_g) \approx \xi^k [1-\xi]^{N_g-k}[1-(1+j^{-1})^k \delta^k]^{N_e-j} \quad (3)$$

where $$\xi = j\delta^{(j-1)} - (j-1)\delta^j \quad (4)$$

Therefore, the average number of maximal δ-valid jk-patterns in V is $$N_{jk} = N_t P_\delta(j,k,N_e,N_g),$$

where $$Nt = \binom{N_g}{k} x \binom{N_e}{j} \quad (5)$$

Where Nt is the total number of ways in which one can choose a gene and experiment vector. In Equation (3), an approximation is made that is valid when δ is small. This is consistent with the values used in the experimental section, typically δ≦0.25.

The previous observations can be used to assess the statistical significance of a pattern in the phenotype set with respect to the randomized control set. Using classical statistics reasoning, maximal δ-valid jk-patterns are rejected that would be likely to occur in the randomized control set. Under the null hypothesis, the probability $p_{jk}$ that one or more jk-patterns occur in the phenotype set is (this assumes that the number of patterns is distributed according to a Poisson distribution, which is a reasonably good approximation to the actual distribution):

$$i\, pjk = 1 - e^{-N_{jk}}. \quad (6)$$

This will be the p-value or significance level of the preferred statistical test used herein. Thus, setting a reasonable threshold $P_0$, it is possible to say that if one or more jk-patterns in the phenotype set are observed with $p_{jk} < P_0$, the null hypothesis is rejected and a conjecture is made that such jk-patterns could be specific of the cell phenotype under study.

In step 270, a discriminant function is built. This step may also entail further refinements to the maximal patterns to create a better discriminant function. The discriminant function determines whether a sample belongs to the phenotype set or the control set. When building the discriminant, it may be beneficial to further process the gene expression patterns discovered in step 260. In particular, promiscuous patterns may be removed if desired. This is discussed in more detail below.

Once the statistically significant patterns are found in the phenotype set, they can be used as classifiers to build a discriminant function. This function should determine whether or not a previously unseen sample, $v=(v_1, \ldots, v_{N_g})$, belongs to the phenotype or the control set. To this end, a model is built for the probability density function of the expression level for each statistically significant pattern $\pi_1$ of the phenotype set. Each i-th gene of $\pi_1$ contributes with a factor $P_i^+(v)$. The probability density $P_i^+$ is chosen to be normally distributed with mean equal to the average of the cluster for the i-th gene and standard deviation $\sigma_i$ estimated from the actual measurements. If the number of actual measurements were too small, then $\sigma_i$ is taken to be $\delta/2$. For samples in the control set, the same gene would be expressed according to a different probability density $P_i^-(v)$. The latter can be built empirically because all the samples in the control set can be used.

On a first order approximation, independence is assumed between genes and the multivariate distribution is taken to be equal to the product of the probability densities of the individual genes, both in the phenotype and in the control set. This assumption is necessary because not enough data exist to construct a realistic multidimensional probability density for either set.

Promiscuous patterns, which arise from correlations in the control set, are likely to play a minor role in the classification as described in the following discussion. To determine if a new microarray sample fits the phenotype model of ajk-pattern $\pi_1$ for the expression values $(v_1, v_2, \ldots, v_k)$ over the k genes that constitute $\pi_1$, it is scored by the logarithm of the ratio of the two probability densities, as described in Welch, B. L., "Note on Discriminant Functions," Biometrika, Vol 31, pp. 218-220, 1939, the disclosure of which is incorporated herein by reference:

$$S_i \log = \left[ P^+ \frac{(v_1, \ldots, v_k)}{P^-(v_i, \ldots, v_k)} \right] \quad (7)$$

$$\approx \sum_{i=1}^{k} \log[P_i^+(v_i)] - \sum_{i=1}^{k} \log[P_i^-(v_i)]$$

Using this score, it can easily be determined whether promiscuous patterns are contained in the set of statistically significant patterns. Patterns with positive values of $S_1$ for samples taken from the control set are considered promiscuous. Next, the statistically significant patterns are preferably assigned a promiscuity index:

$$p_i = \sum_{S_i(v) > 0} S_i(v \in \text{Control Set}), \quad (8)$$

where the sum runs over all the samples in the control set for which $S_1 > 0$. Patterns whose $S_1 < 0$ for all samples in the control set have a promiscuity index of zero. Patterns can now be sorted according to the promiscuity index, with the least promiscuous pattern first.

The next step is to associate each pattern $\pi_1$ with a coverage set, which includes all the samples in the phenotype set $v^{ph}$ with a positive score $S_1(v^{ph}) > 0$. Finally, an optimal set of patterns is preferably selected using a greedy set covering algorithm to optimally cover the phenotype set. This is described in Chvatal, V., "A greedy heuristics for the set covering problem," Math. Opera. Res., Vol 4, pp. 233-235, 1979, the disclosure of which is incorporated herein by reference. The set covering algorithm tries to use the patterns in sort order according to the promiscuity index: The least promiscuous and most covering pattern is chosen first. The smallest subset of patterns whose coverage sets optimally cover the phenotype set is then used for classification purposes. Therefore, if a non-promiscuous set that optimally covers the phenotype set exists, it will be selected over a promiscuous one.

In step 280, the discriminant is used to classify one or more samples. Each sample is a vector of expressions, where each expression corresponds to one gene of the phenotype matrix. The discriminant is used to classify a sample as either in the phenotype set or in the control set. Typically $N_c$ patterns of the subset of patterns are selected, where this value generally ranges between one and three. The score of a previously unclassified sample v is defined as $$S(v) = \max(S_1(v), 1=1, \ldots, N_c). \quad (9)$$

Equation 9 is a preferred discriminant function. The discriminant function basically runs the unclassified sample and each selected gene expression pattern through Equation (7) to determine a value $S(v)$. Given a threshold $S_c$, the sample fits the phenotype model only if $S(v) \leq S_c$. The theoretical false positive (FP) and false negative (FN) probabilities can be easily estimated by integrating $P^-$ and $P^+$ over the region where their ratio is greater or smaller than the threshold. If a single classifier is used, $S_c=0$ minimizes the sum of false positive and false negative probabilities (see Welch, B. L., "Note on Discriminant Functions," Biometika, Chapter 31, pp. 218-220, 1939). In a multivariate model, $S_c$ must be tuned. The parameter $S_c$ is an useful tunable parameter practically since different problem requires different balance between FP and FN.

It should be noted that other discriminant functions may be used. For example, a simple discriminant function could be a vector derived from a gene expression pattern. The vector could contain the average for each gene in the pattern. Additionally, each gene within the pattern will have some standard deviation. An unclassified sample, itself a vector, would then be included in the phenotype if for each gene in the pattern, the respective entry in the sample is within a range described by the average plus or minus a few standard deviations. This would still require the sample vector to be compared with each gene expression pattern. The previously derived discriminant is preferred, however, as it deals with promiscuous patterns and tends to be more sensitive.

Referring now to FIG. 3, this figure shows an exemplary control matrix. The control matrix has columns corresponding to genes and rows corresponding to experiments. Each entry is a gene expression signal that indicates the expression for that gene for that experiment. The experiments are preferably derived from healthy cells and can be chosen from a multitude of different organisms. Each column will contain expressions for this gene. For instance, there are y genes and each gene has x expressions. The x expressions will have some probability density distribution.

It is desirable to determine a measure that can determine whether two expression levels are similar. As previously discussed, the expression level u of the g-th gene, in the control set, is distributed according to a given probability density $P^-_g(u)$. This density is estimated empirically. A sufficient number of samples is required to measure this density with a sufficient degree of accuracy.

Turning to FIG. 4, a possible shape for $P^-_g$, which is discussed in above, is plotted along with four expression values from hypothetical phenotype cells a, b, c, and d: $u_a$, $u_b$, $u_c$ and $u_d$. Although the Euclidean distance between $u_c$ and $u_d$ is smaller than that between $u_a$ and $u_b$, the likelihood of getting the former values by chance is higher because they are very close to the maximum of the expression probability density. In other words, in order to minimize the probability of finding random clusters in the control set, a metric must be chosen such that $u_c$ and $u_d$ would be considered further away than $u_a$ and $u_b$. As discussed above, the present invention renormalizes the expression axis so that the distance between two points on the new axis is equal to the integral of the $P^-_g(u)$ in the previous coordinate system. This is accomplished by defining a new variable v obtained by transforming the original variable u with the non-linear transformation of Equation (1) given above. In this new variable, the corresponding probability density $Q^-_g(v)$ for the control set is uniformly distributed and normalized in the interval [0,1]. In FIG. 4, the probability density is plotted together with the transformed values for $u_a$, $u_b$, $u_c$, and $u_d$. As expected, the Euclidean distance, as defined by Equation 2 given previously, between $u_a$ and $u_b$ is now smaller than that between $u_c$ and $u_d$, which makes them much more likely candidates for a cluster of expressions. These Euclidean distances correspond to the distances between $v_a$ and $v_b$ and between $v_c$ and $v_d$, respectively. The transformation has made the difference between $v_c$ and $v_d$ larger than the difference between $v_a$ and $v_b$. It should be noted that, when transforming a phenotype matrix, each entry in the phenotype matrix will be a u expression signal. The transformation shown in FIG. 4 may be used to transform the u expression signal into an equivalent transformed v expression signal.

Referring to FIG. 5, this figure shows a phenotype matrix prior to transformation. Each column preferably comprises expression signals from certain genes and each row preferably corresponds to an experiment. The number of genes Ng is not necessarily the same as the number of genes Ny in the control matrix of FIG. 3. However, it will usually be the case that the two numbers of genes will be the same. Additionally, a transformation must be derived for a gene from the control data before values corresponding to the gene in the phenotype matrix can be transformed. Thus, Ny will generally be at least as large as Ng. The transformation for each gene is applied to each expression signal in the column that corresponds to that gene. This will create a transformed phenotype matrix from which gene expression patterns may be determined.

Figures 7, 8:
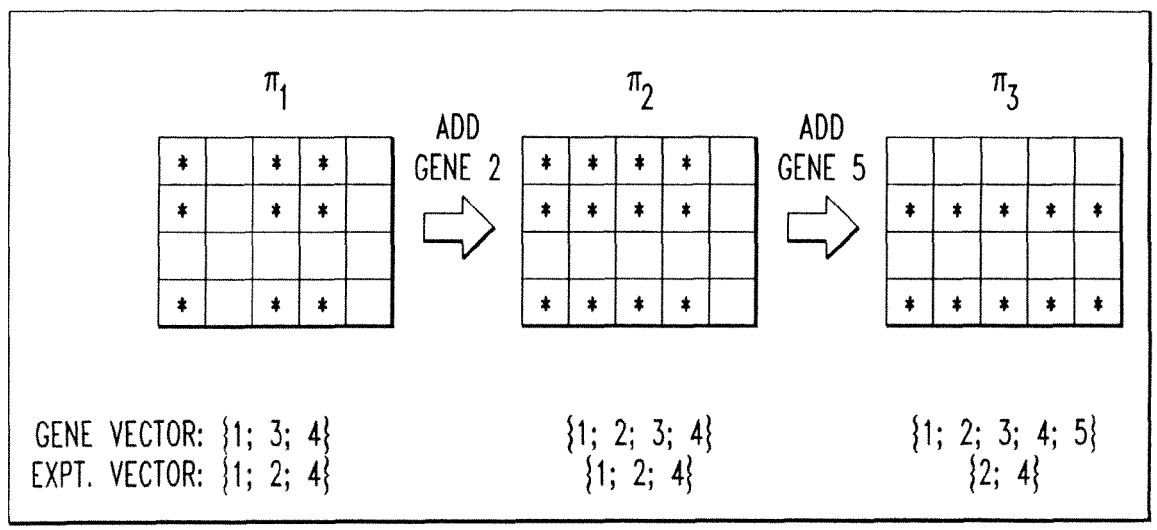
FIG. 7 illustrates a delta-valid but not maximal gene expression pattern in accordance with one embodiment of the present invention.
FIG. 8 illustrates several possible delta-valid gene expression patterns in accordance with one embodiment of the present invention.

Referring to FIG. 6, this figure contains an example transformed phenotype matrix V with $N_g$=5 genes and $N_e$=4 experiments. It is desired that maximal patterns be found for this matrix. Given a gene vector G={1, 3, 4} and an experiment vector E={1, 2, 4}, $V_{G,E}$ is as shown in FIG. 7. $V_{G,E}$ is not a ($\delta$=0.05)-valid (j=3, k=3)-pattern because the values in its second and third column are spread over an interval greater than 0.05. The same pattern, $\pi_1$ in FIG. 8, is ($\delta$=0.1)-valid but not maximal, because adding gene 2 to G, produces $\pi_2$ which is still $\delta$-valid. Pattern $\pi_2$ is maximal because adding any other gene or experiment yields submatrices that are no longer ($\delta$=0.1)-valid. Pattern $\pi_3$ shows another ($\delta$=0.1)-valid (j=2, k=5)-pattern after adding gene 5 and removing experiment 1. This pattern is also maximal.

Thus, what has been disclosed so far is a system and method that transforms gene expression levels of one phenotype from a probability density to a uniform probability density. The transformation is used to transform expression levels of another phenotype. These transformed values, when placed in a matrix, are used to determine a number of gene expression patterns. The gene expression patterns, which are primarily submatrices of the transformed phenotype matrix, may be used to determine if a sample belongs to the first or second phenotype.

Now that the main aspects of the present invention have been discussed, some examples and experiments will now be related.

EXAMPLES

Affymetrix HU6800 GeneChips have been used to monitor the gene expression levels of 6,817 full length human genes in 60 human cancer cell lines (experiments were performed at the Whitehead Institute), as described in Weinstein, J. N. et al., "An Information-Intensive Approach to the Molecular Pharmacology of Cancer," Science, Vol 275, pp. 343-349, 1997, the disclosure of which is incorporated by reference herein. These are organized into a set of panels for leukemia, melanoma, and cancer of the lung, colon, kidney, ovary, and central nervous system. The identity of the genes is not known. Consequently, they are therefore identified by a numeric identification.

Genes with expression values of 20 or less are considered switched off. From the 6,817 original genes, a subset of 418 was selected by means of a variational filter to eliminate genes that did not change significantly across samples (variational filters were also used in Eisen, M. B. et al., "Cluster analysis and display of genome-wide expression patterns," Proc. Natl. Acad. Sci. USA, Vol 95, pp. 14863-14868, 1998; and Tamayo, P. et al. "Interpreting Patterns of Gene Expression with Self-Organizing Maps: Methods and Application to Hematopoietic Differentiation," Proc. Natl. Acad. Sci. USA, Vol 96, pp. 2907-2912, 1999, the disclosures of which are incorporated by reference herein).

Figure 9:
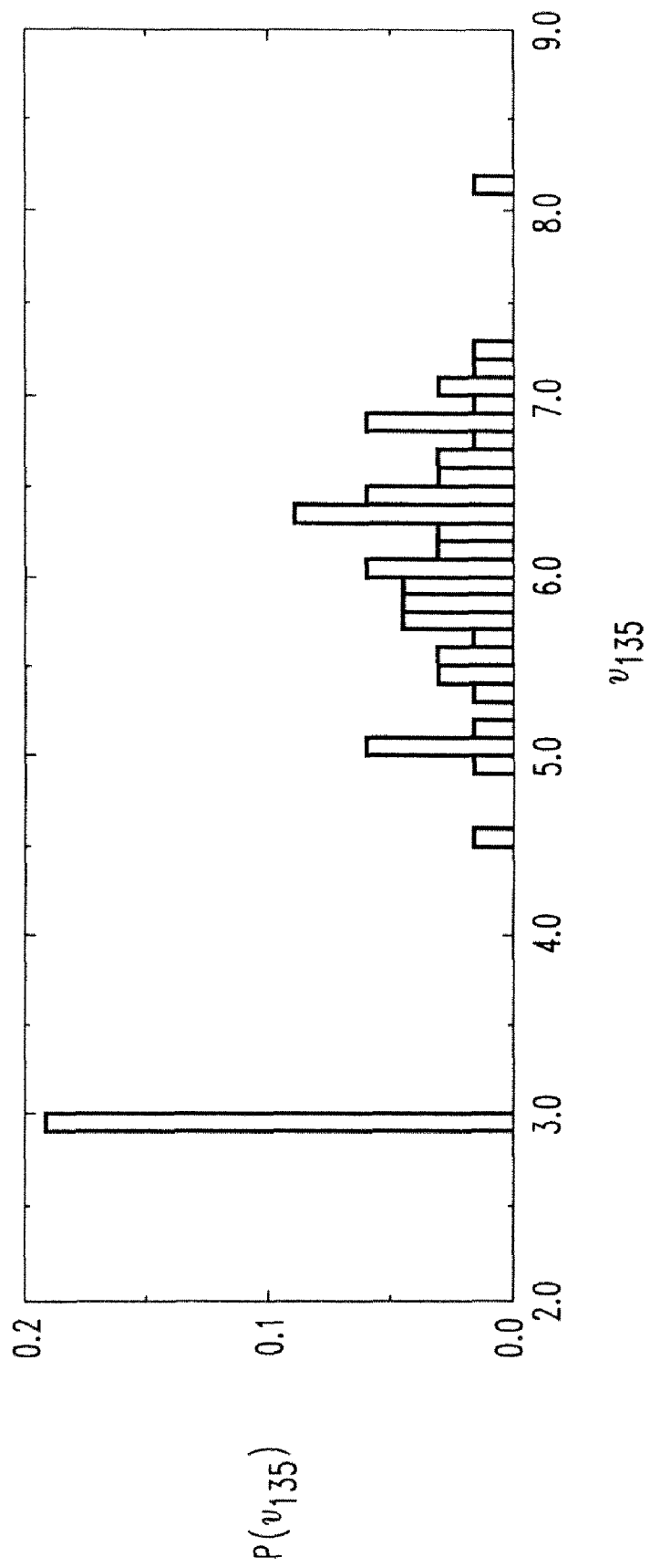
FIG. 9 shows a histogram of the log expression of gene 135.
Figure 10:
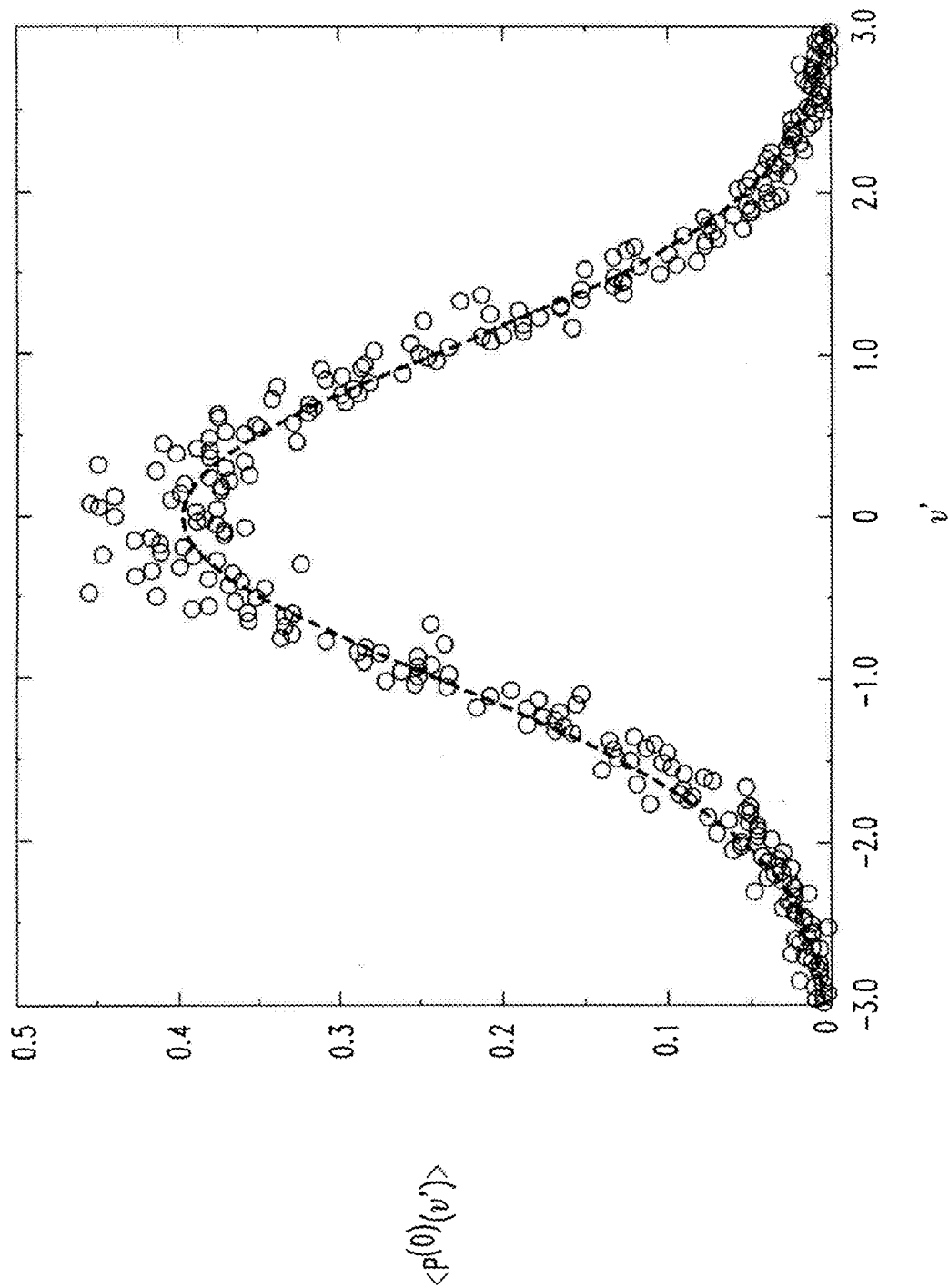
FIG. 10 shows a graph of normalized probability density for a number of full length human genes in 60 human cancer cell lines.

The fluorescence intensity $\phi_g$ of each gene, roughly proportional to the mRNA concentration, appears to be lognormally distributed. The value of variable u is then chosen as $u=\log(\phi_g)$. In FIG. 9, the histogram of a typical expression level of a gene over the 60 samples is shown. This distribution is clearly bimodal. There is a peak at the basal level, corresponding to the gene being switched off in some experiments. The non-basal expression values, on the other hand, are distributed with a well behaved mean and standard deviation. Thus, the corresponding probability density may be written as:

$$P_i^-(u_i) = a_i \delta(u_i - u_0) + (1 - a_i) P_i^{(0)}(u_i), \qquad (10)$$

where $a_i$ is the percentage of expression data being at the basal level $u_0$ and $P_i^{0}(u_i)$ is the density function for the non-basal expression values. For each gene, it is possible to determine its basal level $a_i$, the mean $\bar{u}_i$, and standard deviation $\sigma_i$ of its non-basal density $P_i^{(0)}(u_i)$. Non-basal values of $u_i$ are normally distributed in accord with the observed lognormal distribution of the $\phi_i$. This is shown in FIG. 10, which shows a plot of the combined distribution obtained by shifting and resealing the nonbasal activity of each gene as u'=(ui−$\bar{u}_i$)/$\sigma_i$. The change of variables corresponding to Equation (1) is:

$$v_i = \int_{u_0}^{u_i} P_i^-(x)dx = a_i H(u_i - u_0) + (1-a_i)\int_{u_0}^{u_i} P_i^{(0)}(x)dx. \quad (11)$$

In Equation (11), H(x) is the Heaviside function, which is the function H(x≧0)=1 and H(x<0)=0. This results from the integration of the delta function in the $u_i$ distribution. For $a_i \neq 0$, different values of $u_i$ can correspond to the same value of $v_i$. This is not a problem unless $a_i$ is of the same order of δ, in which case the values at $u_0$ the would not be discriminative are discarded.

Phenotype Analysis Given a gene expression matrix V, with renormalized values $v_{lm}$, the pattern discovery algorithm SPLASH was used to find all maximal δ-valid jk-patterns for k≧4 and j≧4. These parameters were chosen because patterns with too few genes are not specific enough, while patterns with too small a support do not characterize a significant consensus in the data set. The δ was chosen between 0.05 and 0.15, depending on the data sets, such that a sufficient number of patterns is discovered. Typically, this would be on the order of 10 to 50 statistically significant patterns. Larger values of δ are possible, but they increase the probability of finding promiscuous pattern and reduce performance. In general, the smaller value of δ one can choose and still discover patterns, the better the results. The threshold of significance $P_0$ is chosen to be $10^{-4}$.

Below, experimental results are discussed on the classification of 7 samples in the melanoma panel, of 17 samples with mutations in the p53 gene, and of 10 samples whose growth is highly inhibited by the drug Chlorambucil. For each experiment, a plot of the sum $P_{Tot}=p_{FP}+p_{FN}$ of false positives and false negative probabilities as a function of the matching threshold $S_c$ is shown.

Three methods are studied: The pattern discovery method (PD) of the present invention; the support vector machine (SVM) method disclosed in Brown, M. P. S. et al., "Support Vector Machine Classification of Microarray Gene Expression Data," University of California Technical Report USCC-CRL-99-09, 1999; and the gene by gene method (GBG) disclosed in Golub, T. R. et al., "Molecular Classification of Cancer: Class Discovery and Class Prediction by Gene Expression Monitoring," Science, Vol 286, pp. 531-537, 1999. For each given phenotype, its complement in the NCI-60 was used, excluding the samples whose phenotype cannot be accurately determined (neutral samples), as the control set.

Given the limited number of samples in the NCI-60 set, false positive and false negative ratios were computed by cross validation. Each sample both in the phenotype and in the control set was removed in turn. The present invention was trained using the remaining samples, and this included gene axis transformation, pattern discovery, and set covering. Finally, the previously removed sample was classified as described in regards to step 280. When a phenotype set sample was misclassified it was considered a false negative. When a control sample was misclassified it was considered a false positive. All computation times reported are relative to a 450 MHZ PENTIUM II, where a PENTIUM is a trademark for a computer processor. In FIGS. 11 through 14, the sum of the false positive and false negative probabilities is plotted as a function of the classification score threshold. PD is shown by a thick solid line, SVM by a dashed line with diamonds, and GBG by a dotted line with circles.

Melanoma

Figure 11:
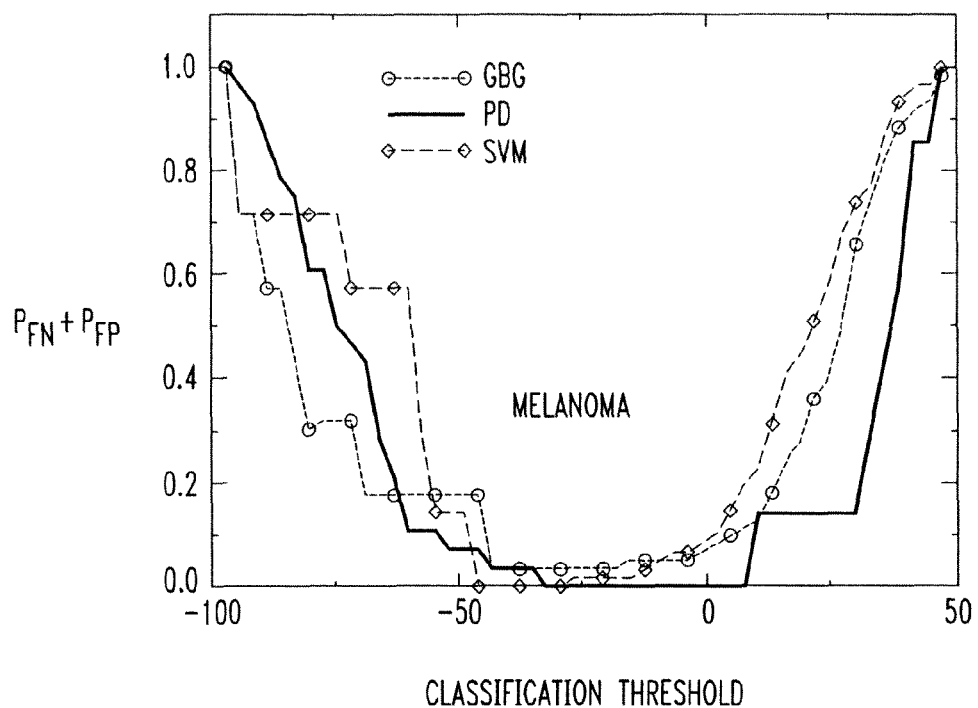
FIG. 11 shows a graph of experimental results, using three different methods including a method of the present invention, for the classification of 7 samples of melanoma.

The melanoma panel included 7 samples. There were also 14 neutral samples. These were selected by biologists prior to this analysis. When the complete set of melanoma samples was used for the training, there was only one statistically significant gene expression pattern that was selected after the set covering phase. FIG. 11 shows the performance of the complete analysis, with δ=0.12, as described in the previous section. Both SVM and PD show a significant range of the match threshold $S_c$ where both false positive and false negative probabilities are zero. This is considered perfect recognition. The GBG produces results which are very similar, although a fraction less accurate. The time required to classify a sample with the PD method is approximately 10 seconds.

p53 Mutation

Figure 12:
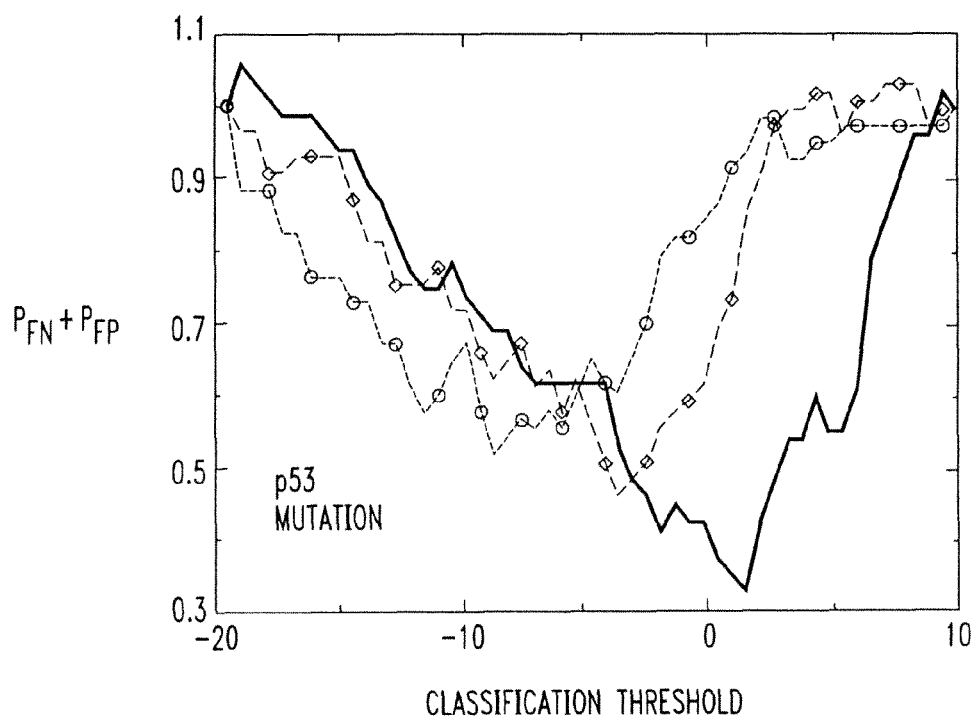
FIG. 12 shows a graph of experimental results, using three different methods including a method of the present invention, for the classification of 17 cancer samples with mutations in the p53 gene.

A more challenging phenotype is that of 17 samples for cells with mutations in the p53 gene. The corresponding set of cancer morphologies is considerably more complex. It includes 5 melanoma, 3 renal cancer samples, 2 samples for cancer of the central nervous system, leukemia, ovarian cancer, and breast cancer, and 1 sample for colon cancer. As mentioned earlier, this is likely to have several sub-phenotypes at the molecular level. This is confirmed by this analysis, which also highlights a much wider range of variability for the various methods. As shown in FIG. 12, the GBG method performs quite poorly with a min($p_{Tot}$)=0.51. The SVM method improves on that result, bringing that value to about 0.46. The present method, with δ=0.12, has the best result at min($p_{Tot}$)=0.33. Three distinct, rather orthogonal patterns are used on average for each sample classification. If only one pattern is allowed, results become close to that of the SVM method. The time required to classify a sample with the PD method is approximately 20 seconds.

Chlorambucil GI 50

Figure 13:
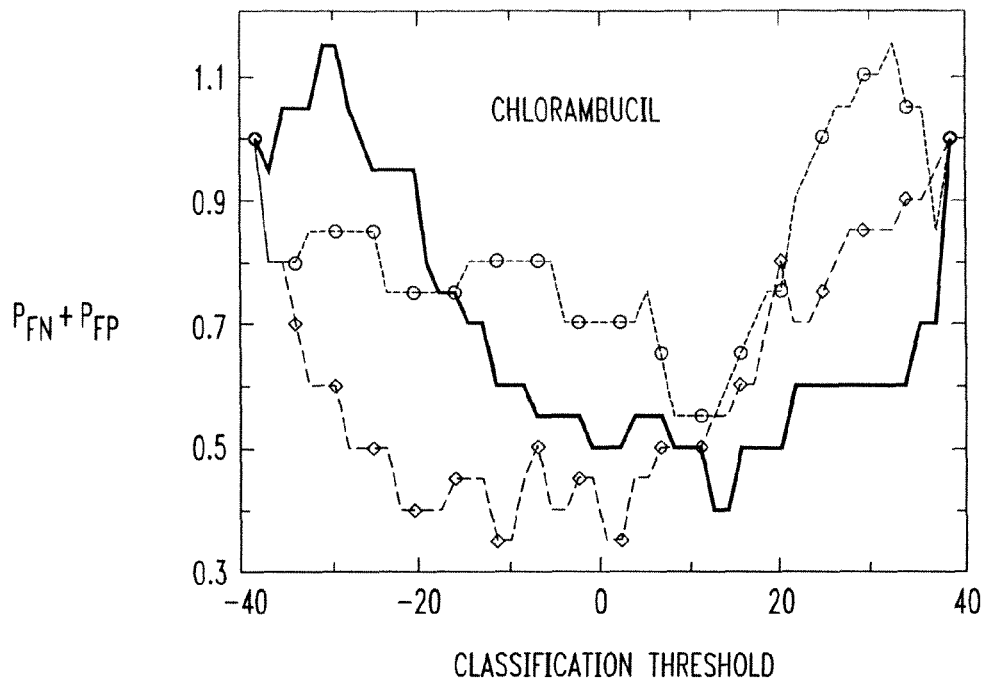
FIG. 13 shows a graph of experimental results, using three different methods including a method of the present invention, for the classification of 10 cancer samples whose growth is highly inhibited by the drug Chloramucil.

Some truly interesting phenotypes are associated to the ability of a given drug to inhibit cell growth. These are relevant because many experimental anti-cancer compounds exhibit relatively poor growth inhibition rates across large variety of cancer cells of similar morphology. If it were possible, however, to correlate the effectiveness of a compound to the much richer space of the gene expression profile of a cell, it could be possible to determine a priori which cells are most likely to be inhibited by a drug. To test this scenario, Chlorambucil (NSC 3088) was selected from the NCI anti-cancer database. Since the growth inhibition rate is distributed rather continuously over the entire NCI-60 spectrum, the samples were split into three groups. The phenotype group contained the 10 cells that are most inhibited by Chlorambucil. The control group contained the 20 samples whose growth is least inhibited by the compound. The third set of 30 cells is considered neutral. As shown in FIG. 13, the SVM and PD methods perform similarly, with a slight advantage towards the former. Best values for $p_{Tot}$ are 0.35 and 0.4 respectively. For the PD method, a value of δ=0.12 is used. The other method cannot do better than 0.55. The time required by the PD method to classify a sample is 10 seconds.

Synthetic Data Analysis

Figure 14:
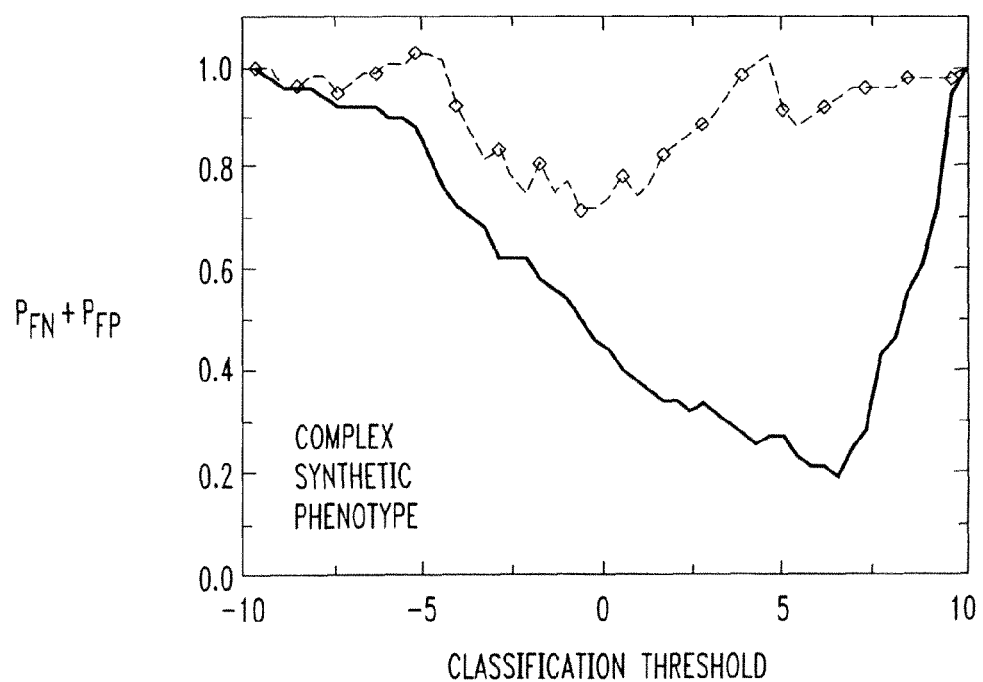
FIG. 14 shows a graph of experimental results, using two different methods including a method of the present invention, for the classification of a complex synthetic phenotype.

Several cross-validation checks using synthetic or randomized data have been performed to validate the present invention and its approach. Three synthetic data sets were analyzed. The first test was designed to evaluate the theoretical performance of the algorithms in the case of phenotype mixtures. A synthetic data model was generated with the same gene by gene statistics as the control set for the p53 study. A set of 48 control samples was generated from this model at random. Their gene-by-gene probability density was virtually identical to that of the real control set in the p53 study. A set of 18 phenotype samples was synthetically generated. This set consisted of three independent sub-phenotypes of 6 samples each. Each sub-phenotype was characterized by 10 marker genes clustered around a tight interval. Remaining genes were modeled as in the control set. Marker genes were different for different sub-phenotype with some overlap. In particular, sub-phenotype 1 and 2 had 6 marker genes in common; sub-phenotype 2 and 3 had 2 marker genes in common. Marker genes were expressed differently than in the control according to the following criteria: 1) they were given a different mean located about $0.5\sigma$ away from the control mean, 2) they were given a smaller standard deviation $0.33\sigma$, where $\sigma$ is the standard deviation of the same gene in the control set. As shown in FIG. 14, there was a dramatic difference between the performance of the SVM method and that of the PD method. The minimum of $p_{Tot}$ was about 0.7 for the SVM method and 0.19 for the PD method. About 80% of the genes composing the sub-phenotypes are correctly identified by the 3 resulting patterns. This seems a good indication that the PD method is a suitable choice for the classification of some complex phenotypes that may be mixtures of simpler sub-phenotypes.

Figure 15:
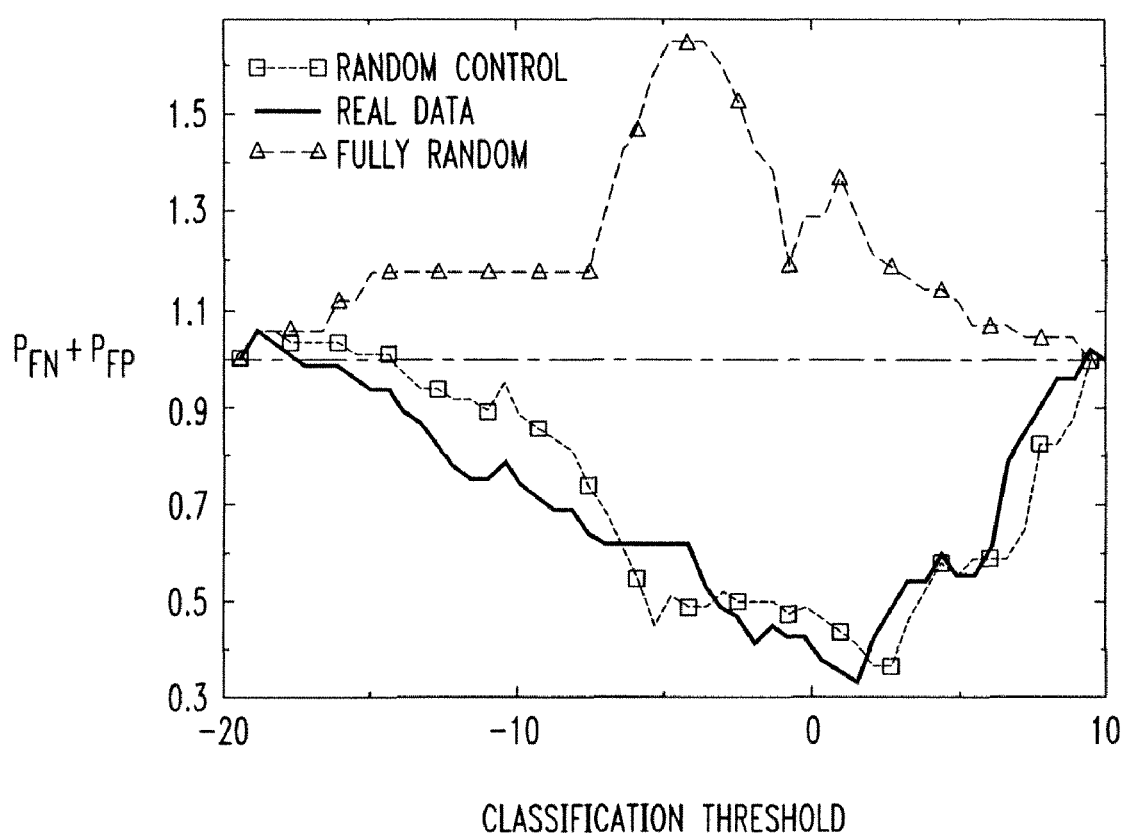
FIG. 15 shows a graph of experimental results, using a method of the present invention, for the classification of real, random control, and fully random data.

The second synthetic data set was designed to determine whether correlation of genes in the control set is a significant factor and could reduce the performance of the technique. To accomplish this goal, the values of the genes have been randomly permuted only across the control set on a gene by gene basis. This has the effect of leaving the expression probability density for each gene for the control virtually unchanged, while removing any possible correlation between the values of genes in the same sample. Results for the classification are shown in FIG. 15, as shown by a dashed line with squares. There are no major differences with respect to the same curve for the real data of FIG. 12, which is reproduced in FIG. 15 as the thick solid line. This proves that correlation in the genes, even though present in the data, does not result in classifiers that are highly correlated over the control set.

Finally, a test was designed to determine whether this approach may suffer from over-fitting the data. To that end, classification was performed using the same data and criteria as for the p53 phenotype study but after the expression values of the individual genes have been randomly permuted across all the samples on a gene by gene basis. The results of the classification are shown in a dashed line with triangles in FIG. 15. As clearly shown, performance was very poor, with a value of $p_{Tot}$ consistently larger than 1 over the entire classification threshold interval. The PD method, as well as the SVM and GBG methods, exhibits no predictability for these data sets. In other words, the sum of the false positive and the false negative rates is close to 1, as it should be Thus, results for the classification of melanoma, p53 mutations and the GI 50 activity of Chlorambucil are excellent. They range from 0% to about 40% sum of false positive and false negative probability. The high sensitivity and specificity of the present method for complex phenotypes such as p53 show that the method can successfully deal with multiple independent sub-phenotypes. Moreover results from one of the first attempts to predict drug effectiveness from gene expression data also are very good. The present invention is especially well suited to treat complex phenotypes, composed of several sub-phenotypes. This has been shown for the p53-related phenotype and for a synthetic data set.

The present invention has better predictive power than other methods. Another advantage of the present method over SVM is that the present method highlights the relevant marker genes, their expression range in the phenotype, and the independent patterns that relate them. Such information is highly desirable for discovering the mechanism for various diseases at the molecular level. The SVM method, on the other hand, is more like a black box for classification.

It is to be understood that the embodiments and variations shown and described herein are merely illustrative of the principles of this invention and that various modifications may be implemented by those skilled in the art without departing from the scope and spirit of the invention. For instance, other suitable pattern searching methods may be used, and other discriminant functions may be designed and used.

What is claimed is:

1. A method for the characterization of phenotypes by gene expression patterns and classification of samples based thereon, wherein the method is run on a system comprising one or more distinct devices, each of the one or more distinct devices being embodied on a tangible computer-readable recordable storage medium, the method comprising:

a) forming, from a plurality of first genes and first samples of a first phenotype, a first matrix of gene expression signals for the first phenotype, each gene expression signal corresponding to one of the first genes and one of the first samples, wherein forming a first matrix of gene expression signals for the first phenotype is carried out by a data storage device executing on a hardware processor;

b) forming, from a plurality of selected genes and selected samples of a selected phenotype, a second matrix of gene expression signals for the selected phenotype, each gene expression signal corresponding to one of the selected genes and one of the selected samples, wherein each selected gene corresponds to one of the first genes, wherein forming a second matrix of gene expression signals for the selected phenotype is carried out by a data storage device executing on a hardware processor;

c) deriving a plurality of transformations, wherein each transformation transforms a probability density distribution of gene expression signals within a selected interval of the gene expression signals for one of the first genes to a uniform probability density distribution of gene expression signals, whereby each transformation corresponds to a selected gene, wherein deriving a plurality of transformations is carried out by a data storage device executing on a hardware processor;

d) applying, for each of the selected genes, one of the transformations to the gene expression signals of a corresponding one of the selected genes of the second matrix, wherein applying one of the transformations to the gene expression signals of a corresponding one of the selected genes of the second matrix is carried out by a data storage device executing on a hardware processor; and e) defining at least one submatrix of the second matrix, wherein each transformed gene expression signal for each gene of the submatrix falls within a selected range, wherein defining at least one submatrix of the second matrix is carried out by a data storage device executing on a hardware processor.

2. The method of claim 1, wherein a number of first genes is the same as a number of selected genes.

3. The method of claim 1, wherein a number of selected genes is less than a number of first genes.

4. The method of claim 1, wherein each of the at least one submatrices is a largest distinct submatrix that satisfies step (e).

5. The method of claim 4, wherein the at least one submatrix comprises a plurality of submatrices.

6. The method of claim 1, wherein step (c) comprises the steps of, for each of the transformations:
   i) determining a function that approximates the distribution of expression levels for a corresponding one of the first genes; and
   ii) using the function to create the transformation corresponding to the one first gene, wherein the transformation renders uniform a probability distribution of the transformed gene expression signals, and wherein each gene expression signal is mapped by the transformation into a transformed gene expression signal.

7. The method of claim 6, wherein step (d) comprises the steps of:
   i) selecting a gene expression signal in the second matrix;
   ii) selecting one transformation that corresponds to the gene expression signal;
   iii) determining a transformed gene expression signal by using the one transformation and the gene expression signal; and
   iv) performing the preceding three steps, selecting another gene expression signal each time, until all of the gene expression signals have been selected and their respective transformed values determined.

8. The method of claim 1, wherein each of steps (a) and (b) comprises a step of depositing biological material from an organism upon a gene expression array.

9. The method of claim 8, wherein the biological material comprises a marker substance operable to exhibit a perceptible gene expression signal for indicating a relationship between a gene element and the biological material.

10. The method of claim 9, wherein the marker substance is operable to exhibit fluorescence as the perceptible gene expression signal.

11. The method of claim 1, further comprising the steps of:
   f) determining a gene expression signal from biological material of an organism for each gene of each of the at least one submatrices; and
   g) determining a deviation of each of the gene expression signals of the organism from the selected range of each selected gene in the at least one submatrix.

12. The method of claim 11, further comprising the step of:
   h) determining if the deviation of each of the gene expression signals from the biological material of the organism meets predetermined criteria, whereby the organism exhibits the selected phenotype if the deviation of each of the gene expression signals meets the predetermined criteria.

13. The method of claim 12: wherein the at least one submatrix comprises a plurality of submatrices, and wherein:
   step (f) comprises the step of forming an organism vector from the gene expression signals from the biological material of the organism;
   step (g) comprises the steps of:
      i) selecting at least one of the plurality of submatrices;
      ii) converting each of the at least one selected submatrices to a vector; and
      iii) using the vectors for each of the selected submatrices in a discriminant function to compare the vectors from the submatrices to the organism vector; and
   step (h) comprises the step of determining if the discriminant function returns a value greater than a threshold.

14. A system comprising: a memory that stores computer-readable code; and a processor operatively coupled to the memory, the processor configured to implement the computer-readable code, the computer-readable code configured to:
   form, from a plurality of first genes and first samples of a first phenotype, a first matrix of gene expression signals for the first phenotype, each gene expression signal corresponding to one of the first genes and one of the first samples;
   form, from a plurality of selected genes and selected samples of a selected phenotype, a second matrix of gene expression signals for the selected phenotype, each gene expression signal corresponding to one of the selected genes and one of the selected samples, wherein each selected gene corresponds to one of the first genes;
   derive a plurality of transformations, wherein each transformation transforms a probability density distribution of gene expression signals within a selected interval of the gene expression signals for one of the first genes to a uniform probability density distribution of gene expression signals, whereby each transformation corresponds to a selected gene;
   apply, for each of the selected genes, one of the transformations to the gene expression signals of a corresponding one of the selected genes of the second matrix; and
   define at least one submatrix of the second matrix, wherein each transformed gene expression signal for each gene of the submatrix falls within a selected range.

15. The system of claim 14, wherein the computer-readable code is further configured to:
   determine a gene expression signal from biological material of an organism for each gene of each of the at least one submatrices; and
   determine a deviation of each of the gene expression signals from the biological material of the organism from the selected range of each selected gene in the at least one submatrix.

16. The system of claim 14, wherein the computer-readable code is further configured to determine if the deviation of each of the gene expression signals from the biological material of the organism meets predetermined criteria, whereby the organism exhibits the selected phenotype if the deviation of each of the gene expression signals meets the predetermined criteria.

17. An article of manufacture comprising: a tangible computer readable recordable storage medium having computer readable code means embodied thereon, the computer readable program code means comprising:
   a step to form, from a plurality of first genes and first samples of a first phenotype, a first matrix of gene expression signals for the first phenotype, each gene expression signal corresponding to one of the first genes and one of the first samples;
   a step to form, from a plurality of selected genes and selected samples of a selected phenotype, a second matrix of gene expression signals for the selected phenotype, each gene expression signal corresponding to one of the selected genes and one of the selected samples, wherein each selected gene corresponds to one of the first genes;

a step to derive a plurality of transformations, wherein each transformation transforms a probability density distribution of gene expression signals within a selected interval of the gene expression signals for one of the first genes to a uniform probability density distribution of gene expression signals, whereby each transformation corresponds to a selected gene;

a step to apply, for each of the selected genes, one of the transformations to the gene expression signals of a corresponding one of the selected genes of the second matrix; and a step to define at least one submatrix of the second matrix, wherein each transformed gene expression signal for each gene of the submatrix falls within a selected range.

18. The article of manufacture of claim 17, wherein the computer-readable code means further comprises:

a step to determine a gene expression signal from biological material of an organism for each gene of each of the at least one submatrices; and a step to determine a deviation of each of the gene expression signals from the biological material of the organism from the selected range of each selected gene in the at least one submatrix.

19. The article of manufacture of claim 17, wherein the computer-readable code means further comprises a step to determine if the deviation of each of the gene expression signals from the biological material of the organism meets predetermined criteria, whereby the organism exhibits the selected phenotype if the deviation of each of the gene expression signals meets the predetermined criteria.

20. The article of manufacture of claim 17, wherein a number of first genes is the same as a number of selected genes.

* * * * *